United States Patent [19]

Sturino

[11] Patent Number: 5,713,886
[45] Date of Patent: Feb. 3, 1998

[54] PANTY LINER

[76] Inventor: David P. Sturino, 1224 Diamond Cove, El Paso, Tex. 79912-1270

[21] Appl. No.: 742,875

[22] Filed: Nov. 1, 1996

[51] Int. Cl.$^6$ .................................................. A61F 13/15
[52] U.S. Cl. ...................... 604/390; 604/385.1; 604/387
[58] Field of Search .............................. 604/385.1, 385.2, 604/386, 387, 389, 390

[56] References Cited

U.S. PATENT DOCUMENTS

| | | |
|---|---|---|
| 3,570,491 | 3/1971 | Sneider. |
| 3,881,490 | 5/1975 | Whitehead et al.. |
| 4,327,732 | 5/1982 | Thinnes ................................... 604/385.1 |
| 4,536,181 | 8/1985 | Cook. |
| 5,037,417 | 8/1991 | Ternström et al.. |
| 5,291,617 | 3/1994 | Moretz et al.. |
| 5,439,458 | 8/1995 | Noel et al.. |
| 5,626,572 | 5/1997 | Ahr et al. ................................. 604/387 |

*Primary Examiner*—John G. Weiss
*Assistant Examiner*—K. M. Reichle
*Attorney, Agent, or Firm*—Stephen R. Greiner

[57] ABSTRACT

A sanitary napkin or panty liner especially for use with G-string and thong type undergarments. The panty liner includes an absorbent core having first and second portions. The opposed sides of the second portion flare continuously from the sides of the first portion so that the second portion has, at all points along its length, a transverse width greater than that of the first portion. A casing surrounds the absorbent core. One flap extends laterally from the casing adjacent the first portion of the absorbent core. Another flap extends laterally from the casing adjacent each of the opposed sides of the second portion of the absorbent core. An adhesive strip is secured to each of the flaps for attachment to an undergarment.

19 Claims, 1 Drawing Sheet

PANTY LINER

FIELD OF THE INVENTION

The present invention relates generally to means for collecting body fluids and, in particular, to an externally-applied, absorbent pad therefor.

BACKGROUND OF THE INVENTION

Sanitary pads, napkins, and the like have long been used to absorb the monthly menstrual flow of women. While such products are generally satisfactory in accomplishing this result, they are considered by some to be too large and cumbersome for use with undergarments, such as G-strings and thongs, having narrowed crotch portions. It has also been noted that the adhesive strips which serve to secure the commercially-available sanitary pads or napkins within the "average" undergarment are not located for stable attachment to an undergarment having a narrowed crotch. Thus, the pad or napkin may undesirably move from its original location of attachment during use.

SUMMARY OF THE INVENTION

In light of the problems associated with the prior art pads and napkins for feminine hygiene, it is a principal object of the invention to provide a sanitary pad, napkin or panty liner adapted for nonsliding attachment within an undergarment, such as a G-string or thong, having a narrowed crotch portion.

It is another object of the invention to provide a sanitary pad, napkin or panty liner that is relatively small, thin, and unobtrusive and can be worn with tight-fitting, outer garments of all types.

It is an object of the invention to provide improved elements and arrangements thereof in a sanitary pad, napkin or panty liner for the purposes described which is lightweight in construction, inexpensive in manufacture, dependable and fully effective in use.

Briefly, the sanitary pad, napkin or panty liner in accordance with this invention achieves the intended objects by featuring an absorbent core having attached first and second portions enclosed by a casing. The opposed sides of the second portion flare outwardly from the sides of the first portion so that the second portion has, at all points along its length, a transverse width greater than that of the first portion. One flap extends from the casing adjacent the first portion of the absorbent core. Other flaps extend from each of the opposed sides of the second portion of the absorbent core. An adhesive strip is secured to each of the flaps for attachment to an undergarment.

The foregoing and other objects, features and advantages of the present invention will become readily apparent upon further review of the following detailed description of the preferred embodiment as illustrated in the accompanying drawings.

BRIEF DESCRIPTION OF THE DRAWINGS

The present invention may be more readily described with reference to the accompanying drawings, in which.

Similar reference characters denote corresponding features consistently throughout the accompanying drawings.

DETAILED DESCRIPTION OF THE PREFERRED EMBODIMENT

Figure 1:
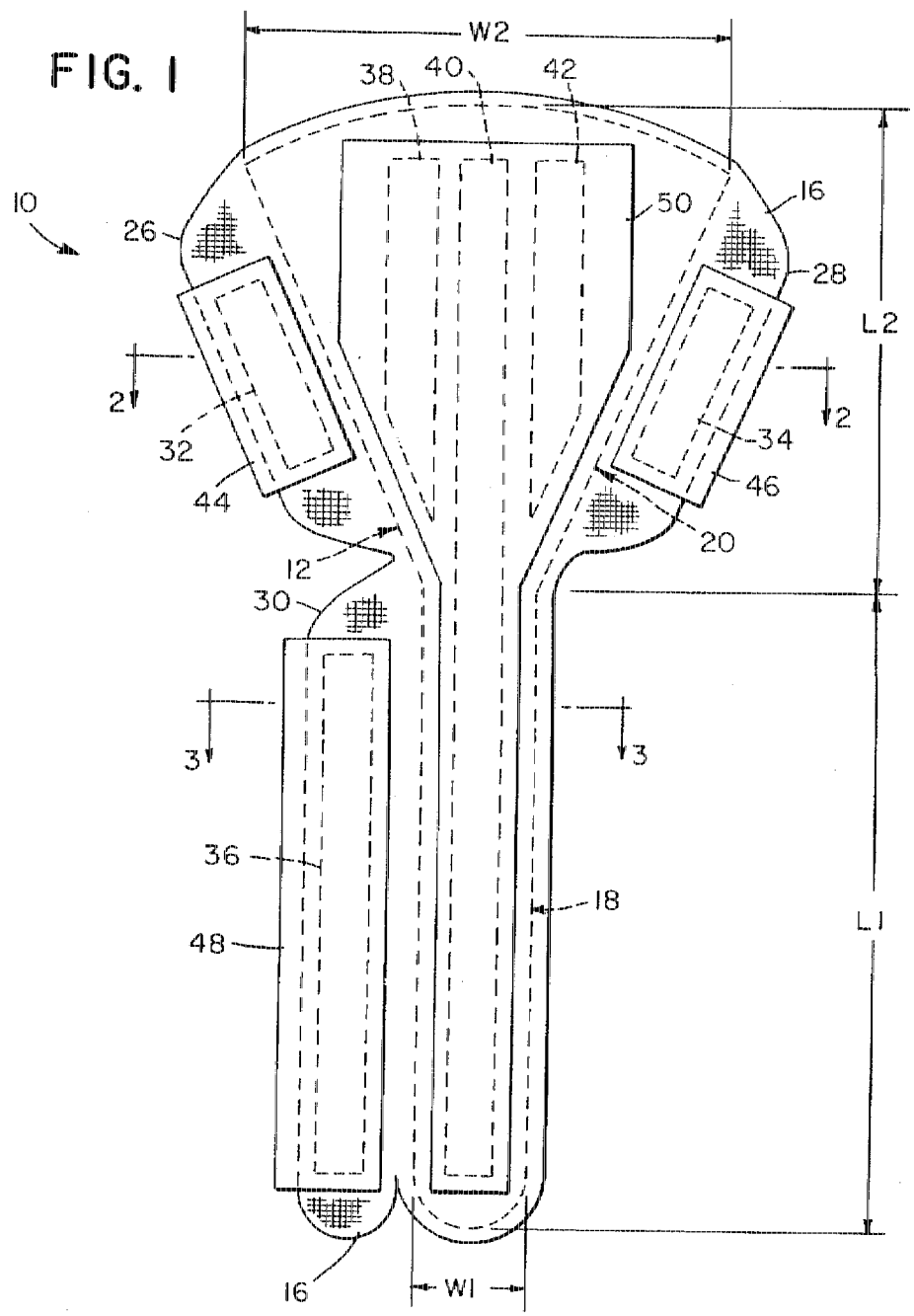
FIG. 1 is a top view of a panty liner in accordance with the present invention.
Figure 2:
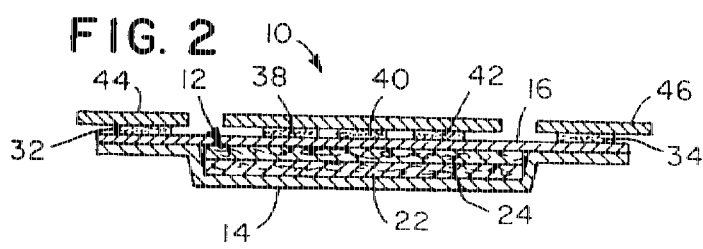
FIG. 2 is an enlarged cross-sectional view taken along line 2—2 of FIG. 1.
Figure 3:
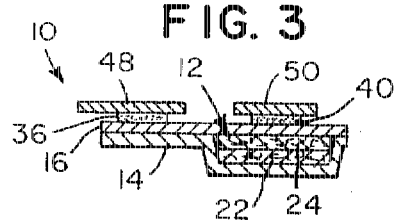
FIG. 3 is an enlarged cross-sectional view taken along line 3—3 of FIG. 1.

Referring now to the FIGS., a sanitary napkin, pad, or panty liner in accordance with the present invention is illustrated at 10. The panty liner 10 includes a multilayered, absorbent body or core 12 positioned between a liquid permeable cover sheet 14 and an impermeable backing sheet 16. The absorbent core 12 is provided with an elongated first end portion 18 having a relatively narrow first end of generally uniform width and a generally triangular second end portion 20 having a relatively wide second end extending therefrom. Alternatively, it may be said that the absorbent core 12 has a pair of opposed side edges extending lengthwise thereof and a pair of opposed intermediate points respectively located on the side edges. The side edges are generally parallel to each other from the first end to the intermediate points and are generally flared outwardly from one another from the intermediate points to the second end. In use, the panty liner 10 is preferably placed in a crotch of an undergarment (not shown) with the relatively-wider end portion 20 disposed toward the front of the undergarment.

The dimensions of the absorbent core 12 are important in ensuring that the panty liner 10 fits snugly within an undergarment having a narrowed crotch portion. The width of the sanitary napkin adjacent the second end is about 3 times the width of the sanitary napkin adjacent the first end. The longitudinal distance from the first end to the intermediate points is about 1.5 times the distance from the second end to the intermediate points. Preferably, the length L1 of the end portion 18 of the absorbent core 12 is about five and one-quarter inches (13.3 cm) whereas the length L2 of the end portion 20 is about three and one-half inches (8.9 cm). The width W1 of the end portion 18 is about one and one-eighth inches (2.9 cm) and the widest width W2 of end portion 20 is about three and one-half inches (8.9 cm). The absorbent core 12 has a thickness in the range of about $\frac{1}{16}$(0.16 cm) inch to about $\frac{1}{4}$inch (0.64 cm).

The absorbent core 12 comprises a transmission layer 22 loosely positioned atop a coextensive storage layer 24. The transmission layer 22 is formed of a low density/high loft material like cotton wadding or wood pulp fiber capable of quickly absorbing and distributing liquids. The underlying storage layer 24, on the other hand, is preferably formed of an absorbent material of similar composition but relatively higher density for trapping liquids therein. The combined thickness of both layers 22 and 24 is about one-sixteenth of an inch (0.16 cm).

The backing sheet 16, preferably a relatively thin film of polyethylene or polyvinyl or any other suitable plastic, provides a moisture barrier for preventing liquids from passing through the panty liner 10. The backing sheet 16 is adhesively bonded to the absorbent core 12 over its entire common surface with the storage layer 24. As the backing sheet 16 has somewhat larger dimensions than those of the absorbent core 12, the backing sheet extends outwardly from all sides of the absorbent core 12 when secured thereto.

The dimensions of the cover sheet 14 coincide with those of the backing sheet 16 so that it too will extend outwardly from all sides of the absorbent core 12 when placed against the transmission layer 22 as shown in the FIGS. Preferably, the periphery of the cover sheet 14, comprising a relatively thin nonwoven, polymeric material such as rayon or any other suitable plastic, is attached by a suitable adhesive or heat sealing to the overlapping portions of backing sheet 16. Thus, the cover sheet 14 itself is not bonded directly to the absorbent core 12 but rather "floats" over such.

After the cover sheet 14 is attached to the backing sheet 16, a cluster of spaced embossments (not shown) may be impressed therein. Between the embossments, the cover sheet 14 is somewhat lofted in rounded, cushion-like contours where unbonded portions of the transmission layer 22 of the absorbent core 12 press against the cover sheet 14. The lofted areas yield a panty liner 10 that is more comfortable to wear.

The attached portions of the cover sheet 14 and the backing sheet 16 are dimensioned to provide the panty liner 10 with side flaps or "wings" 26, 28 and 30 capable of being partially folded around the narrowed crotch portion of an undergarment like a G-string or thong. The wings 26 and 28 extend outwardly from the opposed sides of the triangular second portion 20 of the absorbent core 12. The wing 30, however, extends outwardly from one side of the elongated first portion 18 of the absorbent core 12.

The outside of the backing sheet 16 is provided with spaced-apart adhesive layers 32, 34, 36, 38, 40 and 42 which serve as means for attaching the panty liner 10 to an undergarment. As shown, the adhesive layers 32, 34 and 36 are located, respectively, on the wings 26, 28 and 30. Adhesive layers 38, 40 and 42 are disposed on the backing sheet 16 between the wings 26 and 28. Preferably, the adhesive layers 32–42 comprise a nontoxic, contact-type glue which, after a period of use, may be pulled from an undergarment while leaving no residue on the undergarment.

Removable release liners 44, 46, and 48, respectively, cover the adhesive layers 32, 34 and 36 in order to keep the adhesive from becoming contaminated prior to use. A single release liner 50 covers adhesive layers 38, 40 and 42. The release liners 44–50 are formed of paper having at least one surface treated as with silicone for ready detachment from the adhesive. The release liners 44–50 are retained on the adhesive layers 32–24 until they are detached by an individual as the panty liner 10 is made ready for use.

The panty liner 10 may be made with conventional equipment in a continuous production process. Preferably, the material which is to form the cover sheet 14 is first fed from a roll. (This rolled material has a constant width about one inch 2.54 cm) wider than that of the absorbent core 12 at its widest location W2.) As the cover sheet material is advanced, an absorbent core 12 is cut into the desired shape and then placed on the cover sheet material. Next, the material which is to form the backing sheet 16 is fed from a roll and brought into engagement with the absorbent core 12 and the material which is to form the cover sheet 14.

By means of an adhesive previously applied to the backing sheet material, the backing sheet material is affixed to the absorbent core 12 and to the cover sheet material around the periphery of the absorbent core. After this operation has been completed, the upwardly exposed backing sheet material has adhesive layers 32–42 applied thereto. The panty liner 10 is then cut to shape and is severed from the selvage of the joined backing and cover sheet stock materials.

If the cover sheet 14 is made of plastic material such as nonwoven rayon, it may be heat sealed to the backing sheet 16. In this method of construction, adhesive is not needed to secure the cover and backing sheets 14 and 16 together. Adhesive, however, may still be employed on the storage layer 24 to secure the backing sheet 16 to the absorbent core 12.

Release liners 44–50 are next secured to the adhesive layers 32–42. It is to be noted that the release liners 44–48 extend slightly beyond the sides of the wings 26–30 so that at the time of use the release liners 44?may be easily grasped and pulled from the adhesive layers 32–36.

The panty liner 10 has an overall thickness of about one-eighth inch (0.32 cm) and is capable of bending to conform to the body of a wearer as the wearer either walks or sits. Due to the unique configuration of the absorbent core 12, the panty liner 10 is easily attached to the narrowed crotch portion of an undergarment such as a G-string or thong and is unobtrusive even when a tight-fitting outer garment is worn. After use, the panty liner 10 may be easily removed from the narrowed crotch portion of the undergarment and conveniently discarded.

While the inventive panty liner, sanitary napkin or pad has been described with a high degree of particularity, it will be appreciated by those skilled in the art that numerous modifications and substitutions may be made thereto. Therefore, it is to be understood that the present invention is not limited to the sole embodiment described above, but encompasses any and all embodiments within the scope of the following claims.

I claim:

1. A sanitary napkin, comprising:
   an elongated, absorbent body having a first end and a second end spaced therefrom, said absorbent body further having a pair of opposed side edges extending from said first end to said second end and a pair of opposed intermediate points respectively located on said side edges between said first end and said second end, said side edges being generally parallel to each other from said first end to said intermediate points and being generally flared outwardly from one another from said intermediate points to said second end;
   a first flap extending laterally from one of said side edges of said absorbent body between said intermediate points and said first end;
   a pair of second flaps, each respectively extending laterally from one of said side edges of said absorbent body between said intermediate points and said second end; and,
   a plurality of adhesive strips, one of said adhesive strips being applied to each of said first and second flaps.

2. The sanitary napkin further comprising:
   a liquid pervious cover sheet;
   a liquid impervious backing sheet; and,
   said absorbent body is positioned between said cover sheet and said backing sheet.

3. The sanitary napkin according to claim 1 wherein each of said plurality of adhesive strips is covered with a removable protective sheet.

4. The sanitary napkin according to claim 1 wherein said absorbent body has a thickness in the range of about 1/16 inch to about 1/4 inch.

5. The sanitary napkin according to claim 1 wherein a width of said sanitary napkin adjacent said second end is about three times a width of said sanitary napkin adjacent said first end.

6. The sanitary napkin according to claim 5 wherein a longitudinal distance from said first end to said intermediate points is about 1.5 times a distance from said second end to said intermediate points.

7. A sanitary napkin adapted to be removably mounted in a panty, said sanitary napkin comprising:
   an absorbent core having a first end portion of generally uniform width and a relatively wider second end portion of generally triangular outline integrally formed therewith, said absorbent core further having opposite longitudinal edges extending from said first end portion to said second end portion, said absorbent core further having a top and a bottom;

a liquid pervious cover sheet positioned adjacent said top of said absorbent core and having a first peripheral edge extending outwardly from said opposite longitudinal edges of said absorbent core, said first peripheral edge defining a first flap extending outwardly from one of said longitudinal edges adjacent said first end portion of said absorbent core, said first peripheral edge also defining a pair of second flaps each respectively extending outwardly from one of said opposite longitudinal edges adjacent said second end portion of said absorbent core;

a liquid impervious backing sheet positioned adjacent said bottom of said absorbent core and having a second peripheral edge secured to said first peripheral edge of said cover sheet and being substantially coextensive therewith; and, a plurality of first adhesive strips each being respectively secured to said backing sheet opposite said first and second flaps.

8. The sanitary napkin according to claim 7 wherein each of said plurality of first adhesive strips is covered with a removable protective sheet.

9. The sanitary napkin according to claim 8 further comprising:

a second adhesive strip secured to said backing sheet adjacent said second end portion of said absorbent core; and, a release liner covering said second adhesive strip.

10. The sanitary napkin according to claim 7 wherein said absorbent core has a thickness in the range of about 1/16 inch to about 1/4 inch.

11. The sanitary napkin according to claim 7 wherein a width of the widest portion of said second end portion of said sanitary napkin is about three times a width of said sanitary napkin adjacent said first end portion.

12. The sanitary napkin according to claim 11 wherein a length of said first end portion is about 1.5 times a length of said second end portion.

13. A panty liner, comprising:

an absorbent core including a first portion and an attached second portion, said first portion and said second portion respectively having opposed sides, the sides of said second portion flaring continuously from the sides of said first portion so that said second portion has, at all points along its length, a transverse width greater than a transverse width of said first portion, said absorbent core further having a top and a bottom;

a casing surrounding said absorbent core;

a first flap extending laterally from said casing adjacent one of the opposed sides of said first portion of said absorbent core;

a second flap extending laterally from said casing adjacent each of the opposed sides of said second portion of said absorbent core; and, a plurality of adhesive strips, one of said adhesive strips being secured to each of said first and second flaps.

14. The panty liner according to claim 13 wherein each of said adhesive strips is covered with a removable protective sheet.

15. The panty liner according to claim 13 wherein said first and second flaps are integrally formed with said casing.

16. The panty liner according to claim 13 wherein said casing further includes:

a cover sheet of relatively thin permeable material positioned adjacent said top of said absorbent core; and, a backing sheet or relatively thin impermeable material positioned adjacent said bottom of said absorbent core.

17. The panty liner according to claim 16 wherein said backing sheet is a plastic film.

18. The panty liner according to claim 16 wherein respective peripheries of said cover sheet and said backing sheet are secured together by an adhesive.

19. The panty liner according to claim 16 wherein respective peripheries of said cover sheet and said backing sheet are secured together by heat sealing.

* * * * *